(12) United States Patent
Simard et al.

(10) Patent No.: US 11,911,425 B2
(45) Date of Patent: Feb. 27, 2024

(54) ANTI-AGING COMPOSITION COMPRISING A PLANT EXTRACT

(71) Applicant: IDUNN TECHNOLOGIES, Rosemère (CA)

(72) Inventors: Eric Simard, Rosemère (CA); Vladimir Titorenko, Montréal (CA)

(73) Assignee: IDUNN TECHNOLOGIES, Rosemère (CA)

( * ) Notice: Subject to any disclaimer, the term of this patent is extended or adjusted under 35 U.S.C. 154(b) by 0 days.

(21) Appl. No.: 17/535,804

(22) Filed: Nov. 26, 2021

(65) Prior Publication Data

US 2022/0080007 A1 Mar. 17, 2022

Related U.S. Application Data

(63) Continuation of application No. 15/569,594, filed as application No. PCT/CA2016/050515 on May 5, 2016, now abandoned.

(60) Provisional application No. 62/157,115, filed on May 5, 2015.

(51) Int. Cl.

| | |
|---|---|
| A61K 36/00 | (2006.01) |
| A61K 36/16 | (2006.01) |
| A61K 36/84 | (2006.01) |
| A61Q 19/08 | (2006.01) |
| A61K 31/05 | (2006.01) |
| A61K 31/132 | (2006.01) |
| A61K 31/155 | (2006.01) |
| A61K 31/201 | (2006.01) |
| A61K 36/185 | (2006.01) |
| A61K 36/23 | (2006.01) |
| A61K 36/71 | (2006.01) |
| A61K 36/76 | (2006.01) |
| A61K 8/44 | (2006.01) |
| A61K 8/9771 | (2017.01) |
| A61K 8/9789 | (2017.01) |
| A61P 43/00 | (2006.01) |
| A61K 8/34 | (2006.01) |
| A61K 8/365 | (2006.01) |
| A61K 8/41 | (2006.01) |
| A61K 8/43 | (2006.01) |

(52) U.S. Cl.
CPC ............. *A61K 36/16* (2013.01); *A61K 8/347* (2013.01); *A61K 8/365* (2013.01); *A61K 8/41* (2013.01); *A61K 8/43* (2013.01); *A61K 8/44* (2013.01); *A61K 8/9771* (2017.08); *A61K 8/9789* (2017.08); *A61K 31/05* (2013.01); *A61K 31/132* (2013.01); *A61K 31/155* (2013.01); *A61K 31/201* (2013.01); *A61K 36/185* (2013.01); *A61K 36/23* (2013.01); *A61K 36/71* (2013.01); *A61K 36/76* (2013.01); *A61K 36/84* (2013.01); *A61P 43/00* (2018.01);

*A61Q 19/08* (2013.01); *A61K 2800/5922* (2013.01); *A61K 2800/78* (2013.01)

(58) Field of Classification Search
CPC ...................................................... A61K 31/132
See application file for complete search history.

(56) References Cited

U.S. PATENT DOCUMENTS

| | | | |
|---|---|---|---|
| 6,200,594 | B1 | 3/2001 | Ernest et al. |
| 8,496,979 | B1 | 7/2013 | Hastings et al. |
| 8,747,915 | B1 | 6/2014 | Giampapa |
| 2004/0076691 | A1* | 4/2004 | Haines ............... A61K 36/9066 424/766 |
| 2005/0129783 | A1 | 6/2005 | Mccleary et al. |
| 2005/0271692 | A1 | 12/2005 | Gervasio-Nugent et al. |
| 2006/0040000 | A1* | 2/2006 | Gokaraju ............. A61K 31/726 424/771 |
| 2007/0122502 | A1 | 5/2007 | Logsdon |
| 2009/0196951 | A1 | 8/2009 | Brandborg |
| 2010/0297040 | A1 | 11/2010 | Keefe |
| 2013/0067804 | A1 | 3/2013 | Naidu |

FOREIGN PATENT DOCUMENTS

| | | |
|---|---|---|
| CN | 1109768 | 5/2003 |
| CN | 101352528 | 1/2009 |
| FR | 2858224 | 2/2005 |
| GB | 2516963 | 2/2015 |
| JP | 2002233224 | 8/2002 |
| JP | 2013209651 | 10/2013 |
| WO | 9921006 | 4/1999 |
| WO | 2004093518 | 11/2004 |

OTHER PUBLICATIONS

Carmona et al. "Biology of healthy aging and longevity", Rev Inves Clin. 2016; 68 : 7-16.

Tullet et al. "The SKN-1/Nrf2 transcription factor can protect against oxidative stress and increase lifespan in C. elegans by distinct mechanisms". Aging cell, 2017; 16: 1191-1194.

Cao et al., "Tailor-Made Deep Eutectic Solvents for Simultaneous Extraction of Five Aromatic Acids from Ginkgo biloba Leaves", Molecules. Dec. 5, 2018;23(12):3214.

Baxter, Anti-aging propoerties of reseratrol: review and report of a potent new antioxidant skin care formulation. Journal of Cosmetic dermatology, (2008) vol. 7, No. 1. pp. 2-7.

(Continued)

*Primary Examiner* — Qiuwen Mi

(74) *Attorney, Agent, or Firm* — NORTON ROSE FULBRIGHT CANADA LLP

(57) ABSTRACT

The present description relates to an anti-aging composition comprising at least one plant extract. The composition can comprise at least two different anti-aging agents, wherein one the anti-aging agent is a plant extract. The combination of two anti-aging agents has a superior effect on regulating longevity compared to the use of one anti-aging agent. The plant extract is preferably selected from the group consisting of a Black cohosh extract, a Valerian extract, a *Ginkgo biloba* extract, a Celery seed extract, a White willow extract and a Passion flower extract.

7 Claims, 3 Drawing Sheets

(56) References Cited

OTHER PUBLICATIONS

Nam Sung Min et al. "Valeriana officinalisextract and its main component, valerenic acid, ameliorated-galactose-induced reductions in memory, cell proliferation, and neuroblast differentiation by reducing corticosterone levels and lipid peroxidation", Experimental Gerontology, vol. 48, No. 11, 2013, pp. 1369-1377.
Malva Joao et al. "Neuroprotective properties of Valeriana officinalis extracts", Neurotoxicity Research, Hardwood Academic Publishers, Lausanne, CH, vol. 6, No. 2, 2004, pp. 131-140.
Blagosklonny, Mikhail V, "Answering the ultimate question what is the proximal cause of aging?" Aging, vol. 4, No. 12, 2012.

* cited by examiner

ANTI-AGING COMPOSITION COMPRISING A PLANT EXTRACT

CROSS-REFERENCE TO RELATED APPLICATIONS

This application is a continuation of U.S. application Ser. No. 15/569,594, filed Oct. 26, 2017, which is a National Phase entry of International Application No. PCT/CA2016/050515, filed on May 5, 2016 and claiming priority from U.S. provisional patent application 62/157,115 filed on May 5, 2015, and this application claims priority to and the benefit of the above-identified applications, each of which are incorporated by reference herewith in their entirety.

TECHNICAL FIELD

The present description relates to an anti-aging composition comprising at least one plant extract.

BACKGROUND ART

It is known that aging drives disease. Nearly every major killer disease in developed countries shares a common feature: the risk of getting the disease increases dramatically as you get older. For example, the likelihood of being diagnosed with Alzheimer's disease doubles every five years after the age of 65. A similar kind of relationship can be seen for most types of cancer, heart disease, diabetes, kidney disease, and many others.

The rate of aging may also be measured, and an accelerated rate of aging may be considered 'premature aging', while a slower rate of the aging process may extend health span. It is desirable to maximize the healthy lifespan of cells and organisms and it is also desirable to extend the healthy lifespan by decreasing the rate of aging process and the onset of dysfunctional or disease states. Shortening the lifespan and/or accelerating apoptosis of unhealthy, diseased, damaged, or cancerous cells may also be desirable.

Rather than focussing on curing the individual disease, interventions that target the molecular processes causing aging can simultaneously delay the onset and progression of most age-related disorders (Longo et al., 2015, Aging Cell, 1-14). Such interventions are predicted to have a greater beneficial effect on healthy lifespan than the one that can be attained by treating individual diseases.

Recent discoveries suggest that aging is neither driven by accumulation of molecular damage of any cause, nor by random damage of any kind. Studies in humans and model organisms aimed at elucidating the molecular mechanisms of aging have demonstrated the existence of broadly conserved longevity pathways, and, for the first time, offer real hope of intervening to enhance healthy aging. The best-characterized intervention for delaying aging is dietary restriction (also referred to as caloric restriction). Many studies have shown that a reduced calorie regimen can increase lifespan and delay the onset of multiple age-related phenotypes in a diverse range of organisms, including the entire major model systems used in biomedical research.

Not surprisingly, dietary restriction modulates the activity of multiple cellular factors, several of which have been implicated in longevity and health span. These factors include sirtuins, key metabolic regulators such as AMP kinase, antioxidant enzymes, DNA damage response enzymes, and others. Among these, however, the mTOR signaling pathway, in particular, has emerged as a central pro-aging pathway that is inhibited due to pro-longevity effects of dietary restriction in yeast, nematodes and fruit flies. In response to nutrient depletion, mTOR activity is reduced and this results in a cascade of downstream events that have been shown to promote longevity and enhance resistance to stress. In particular, reduced synthesis of new proteins via inhibition of mRNA translation, enhanced degradation of damaged proteins and other macromolecules via autophagy, and altered carbon metabolism and mitochondrial function all contribute to lifespan extension by dietary restriction.

Although caloric restriction can provide significant benefits, its implementation in humans is unlikely to be achieved. Indeed, to implement such dietary regimen for an adult individual, such individual must limit food consumption to the equivalent of a 5 year old child who is not too active.

Other than dietary restriction, the only non-genetic intervention known to exhibit a significant lifespan-extending effect in yeast, nematodes, fruit flies, and mice is the mTOR-inhibiting drug called rapamycin. However, rapamycin have many negative side effects on an organism, and natural products that inhibit mTOR but lack such negative side effects remain to be identified. Further, dietary restriction is known to have effect not only on mTOR, but also on the AMPK, sirtuins and insulin signaling pathways.

Therefore, the implementation of complex mixtures of several (or many) natural products modulating different signaling pathways is desirable to achieve a more important anti-aging effect.

Classic broad symptoms of aging in mammalian species include increased curvature of the spine (kyphosis), reduced fertility, loss of hearing and eyesight, graying and loss of hair, anemia and immune failure, weight loss, frailty, and loss of cognition. These systemic changes are driven by a variety of molecular, biochemical, and metabolic alterations that occur at the cellular level. A particularly important outcome for cellular aging studies was the use of yeast to discover the conserved genetic pathways that modulate longevity across broad evolutionary distance. Chronological lifespan of yeast cells in stationary culture is the most fruitful model in aging research and numerous papers covering this topic have been published (see for example Kaeberlein, 2010, Nature. 2010 Mar. 25; 464(7288): 513-519).

Humans have evolved to have significantly extended (as compare to most of mammalian species) longevity. Thus, any additional gains in maximum lifespan are likely to be minimal; however, interventions that significantly extend lifespan in model organisms have the potential to extend health span in humans and, therefore, to cause a substantial reduction in morbidity.

The molecular, cellular, organismal and genetic mechanisms that control aging and lifespan have been shown to be highly conserved across millions of years of evolution. Therefore, responses of lower eukaryotic organisms (e.g., *C. elegans, D. melanogaster, S. cerevisiae*) to genetic and pharmacological interventions extending longevity are expected to be similar in mammals including humans. Thus, there is an urgent need in identifying pharmaceutical compositions that mimic aging-delaying effects of dietary/caloric restriction or lifespan-extending genetic mutations.

The budding yeast, *S. cerevisiae*, has been used extensively as a model for cellular aging (Kaeberlein, 2010, Nature, 25: 513-519). Chronological lifespan in yeast is similar to aging of post-mitotic cells, such as mature neurons, adipocytes and mature muscle cells. Yeast chronological aging can be therefore compared to and is predictive of aging of cells and tissues in a human organism. Chronological aging in yeast is assessed by growing a culture of cells to maximal density, at which point nutrients become limiting and cell division arrests. A fraction of cells that can re-enter the cell cycle when exposed to nutrient-rich media is considered to be a fraction of viable cells, and individual cultures are followed until cell viability is close to zero.

While treatments exist for some symptoms of aging-associated disorders, no treatments are currently known that delay aging of the entire organism by targeting multiple cellular and organismal processes with the help of natural extract(s). In addition, by slowing the rate of aging, it may be possible to delay the onset of various diseases/conditions associated with aging.

There is thus still a need to be provided with an anti-aging composition for delaying aging.

SUMMARY

In accordance with the present description there is now provided an anti-aging composition comprising at least two different anti-aging agents, wherein said at least two anti-aging agents are two different plant extracts or one plant extract and a second anti-aging agent, and wherein the at least two anti-aging agents have an superior effect on regulating longevity compared to one anti-aging agent.

It is thus provided an anti-aging composition comprising at least two different anti-aging agents, wherein the at least two anti-aging agents are two different plant extracts or one plant extract and a second anti-aging agent, wherein the plant extract is at least one of a Black cohosh extract, a Valerian extract, a *Ginkgo biloba* extract, a Celery seed extract, a White willow extract and a Passion flower extract, and wherein the at least two anti-aging agents have an superior effect on regulating longevity compared to one anti-aging agent.

It is also provided an anti-aging composition comprising at least one plant extract selected from the group consisting of a Black cohosh extract, a Valerian extract, a *Ginkgo biloba* extract, a Celery seed extract, a White willow extract and a Passion flower extract, and a carrier.

In an embodiment, the second anti-aging agent is resveratrol, metformin, myriocin, or spermidine.

In another embodiment, the plant extract is selected from the group consisting of a Black cohosh extract, a Valerian extract, a *Ginkgo biloba* extract, a Celery seed extract, a White willow extract and a Passion flower extract.

In a further embodiment, the at least two anti-aging agents modulate at least two pathways that regulate longevity.

In a supplemental embodiment, the pathways are TORC1, cAMP/PKA, PKH1/2, SNF1/AMPK or ATG pathways.

In an embodiment, the composition comprises a combination of a Black cohosh extract, and/or a Valerian extract, and/or a *Ginkgo biloba* extract, and/or a Celery seed extract, and/or a White willow extract, and/or Passion flower extract.

In an embodiment, the composition comprises a combination of a Black cohosh extract with a Valerian extract, a *Ginkgo biloba* extract, a Celery seed extract, a White willow extract or Passion flower extract.

In another embodiment, the composition comprises a combination of a Valerian extract with a *Ginkgo biloba* extract, a Celery seed extract or Passion flower extract.

In another embodiment, the composition comprises a combination of a Passion flower extract with a *Ginkgo biloba* extract or a Celery seed extract.

In another embodiment, the composition comprises a combination of a *Ginkgo biloba* extract and a Celery seed extract.

In another embodiment, the composition described herein further comprises resveratrol, myriocin, metformin, or spermidine.

In an embodiment, the composition comprises a Black Cohosh extract and/or Spermidine.

In an embodiment, the composition comprises a Valerian extract with Resveratrol, metformin, myriocin and/or Spermidine.

In another embodiment, the composition comprises a Gingko *biloba* extract and myriocin and/or Spermidine.

In another embodiment, the composition comprises a passion flower extract and resveratrol, metformin, myriocin, and/or spermidine.

In another embodiment, the composition comprises a Celery seed extract and Resveratrol, metformin, and/or myriocin.

In an embodiment, the composition comprises a White willow extract and metformin, myriocin, and/or spermidine.

In a further embodiment, the composition described herein delay the onset and progression of age-related disorders.

In another embodiment, the age-relate disorders are cardiovascular disorders, glycemic disorders, neurodegenerative disorders or osteoporosis disorders.

In another embodiment, the composition described herein is formulated as a cosmetic composition, a dermatological composition, a nutraceutical composition or a pharmaceutical composition.

It is also provided the use of the composition described herein for prolonging longevity of a subject.

It is also provided a method of prolonging longevity of a subject comprising administering to the subject an effective amount of the composition described herein.

BRIEF DESCRIPTION OF THE DRAWINGS

Reference will now be made to the accompanying drawings.

DETAILED DESCRIPTION

Figure 1:
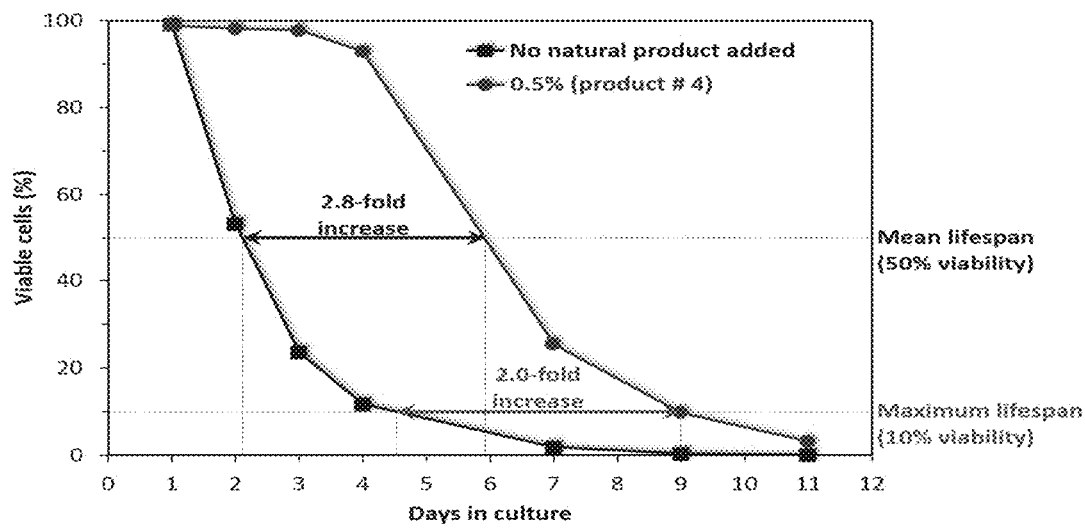
FIG. 1 illustrates mean and maximum lifespan evaluation.

It is provided an anti-aging composition comprising at least one plant extract.

It is also provided an anti-aging composition comprising at least two different anti-aging agents. The anti-aging agents are at least two plant extracts or a combination of one plant extract and a second agent, being for example resveratrol or spermidine. The composition comprising two agents has a superior effect on regulating longevity compared to the use of each individual anti-aging agent.

As described herein, the plant extract is preferably selected from the group consisting of a Black cohosh extract, a Valerian extract, a *Ginkgo biloba* extract, a Celery seed extract, a White willow extract and a Passion flower extract.

In another embodiment, the present disclosure describes the use of at least two different anti-aging agents able to modulate at least two different pathways that regulate longevity to obtain the most important anti-aging effect, said pathways being for example TORC1, cAMP/PKA, PKH1/2, SNF1/AMPK and ATG pathways.

More particularly, it is provided an anti-aging composition comprising at least one plant extract selected from the group consisting of a Black cohosh extract, a Valerian extract, a *Ginkgo biloba* extract, a Celery seed extract, a White willow extract and a Passion flower extract.

A method and composition for delaying the onset of aging process is provided. Described herein are methods and compositions for altering mitochondrial biogenesis and/or mitochondrial maintenance, respiratory efficiency, DNA maintenance, DNA repair, gene expression, and/or gene function, for instance in order to (in various embodiments) reduce and/or retard rate of senescence of a cell, tissue, organ, and/or organism. In example embodiments, this involves altering the maintenance or function of telomeres and telomere structure, the maintenance and control of the cellular responses to oxidative stress and/or oxidative DNA damage, and cellular response to environmental damage or disease or immune response or genetic alteration of cells (see FIG. 3). More specifically, the present description: (i) relates generally to the field of aging process; and (ii) describes novel compositions and methods for using plant extracts or pure chemical compounds, alone or in mixtures and having therapeutic uses in mammals The present description relates to the cosmetic, dermatological, nutraceutical or pharmaceutical (therapeutic) use of natural compounds, in particular as agents that enable prolongation of the lifespan of a cell, i.e. compounds acting as potent anti-aging agents.

The present disclosure relates generally to compounds and methods that enhance survivability and treat and protect cells and animals from injury, disease, and premature death. The composition described herein maximizes the healthy lifespan and/or extend health span. Accordingly, it is encompassed a composition that delay the onset and progression of most age-related disorders, such as for example cardiovascular disorders, glycemic disorders, neurodegenerative disorders or osteoporosis disorders.

Figure 2:
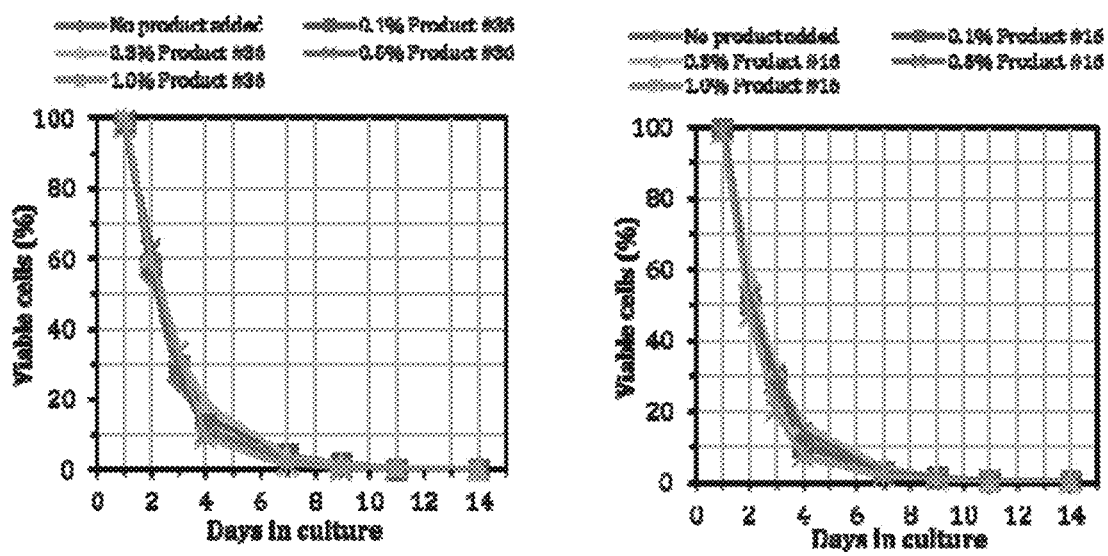
FIG. 2 illustrates a null effect of extracts 36 and 16 on the lifespan of *S. cerevisiae* BY4742.

A total of 59 plant extracts were selected as the one that may potentially have anti-aging effects. FIG. 2 demonstrates examples of 'negative' extracts. Among the 59 plant extracts tested, 6 extracts were found to be positives. More than 10 000 trials were performed to identify such positive extracts, to establish their most efficient longevity-extending concentrations and to demonstrate the beneficial effects in combining them. The extraction process and the commercial source are not limiting factors for the potency of the anti-aging plant extracts described herein.

Data presented herein demonstrates that different anti-aging plant extracts delay aging by targeting different signaling pathways of longevity regulation and/or individual protein components of such pathways. Each of these anti-aging extracts, as well as well-known anti-aging chemical compounds, influences the TORC1, cAMP/PKA, PKH1/2, SNF1/AMPK and ATG pathways that regulate longevity (see FIG. 4). It is thus demonstrated that:

(i) Black cohosh extract (NP #4) delays aging by attenuating the inhibiting effect of the TORC1 signaling pathway on the AMP-activated protein kinase SNF1/AMPK;

(ii) Valerian extract (NP #5) delays aging by mitigating two arms of the pro-aging cAMP/PKA signaling pathway related to the Gh/IGF-1 axis;

(iii) *Ginkgo biloba* extract (NP #8) delays aging by weakening the inhibiting effect of the pro-aging cAMP/PKA signaling pathway on the AMP-activated protein kinase SNF1/AMPK;

(iv) Celery seed extract (NP #12) delays aging by activating the nutrient-sensing protein kinase Rim15, on which the pro-aging TORC1 and cAMP/PKA signaling pathways converge;

(v) White willow extract (NP #21) delays aging by attenuating SCH9, a nutrient-sensory protein kinase known to be activated by the pro-aging TORC1 and PKH1/2 signaling pathways; and (vi) Passion flower extract (NP #6) delays aging not by targeting currently known pro- or anti-aging pathways of longevity regulation; thus, this plant extract inhibits a presently unknown pro-aging pathway and/or activates a presently unknown anti-aging pathway.

The existence of such mechanism for modulating the TORC1, cAMP/PKA, PKH1/2, SNF1/AMPK and ATG pathways by different anti-aging plant extracts as well as by well-known anti-aging chemical compounds implies that multi-component mixtures of some previously unknown anti-aging plant extracts and certain known anti-aging compounds will concomitantly attenuate several pro-aging signaling pathways and activate several anti-aging signaling pathways. Thus, such mixtures should delay aging process to a significantly higher extent than any previously known dietary interventions.

The pairwise mixtures of the many plant extracts described herein extended the mean and maximum lifespans of chronologically aging yeast to significantly higher extent that each of the plant extracts alone.

Aging of multicellular and unicellular eukaryotic organisms is a complex biological phenomenon affecting many cellular processes. These numerous cellular processes are modulated by signaling pathways that are conserved across phyla and include the insulin/insulin-like growth factor 1 (IGF-1), AMP-activated protein kinase/target of rapamycin (AMPK/TOR) and cAMP/protein kinase A (cAMP/PKA) pathways. In yeast, worms, fruit flies and mammals these signaling pathways converge into a network regulating aging process. This network responds to the age-related partial mitochondrial dysfunction and is modulated by mitochondrially produced reactive oxygen species (ROS). By sensing the nutritional status of the whole organism as well as the intracellular nutrient and energy status, functional state of mitochondria, and concentration of ROS produced in mitochondria, the aging process network regulates lifespan and healthspan across species.

In yeast, network regulating longevity includes the following signaling pathways: (1) the pro-aging PKA (protein kinase A) pathway; (2) the pro-aging TORC1 (target of rapamycin complex 1) pathway; (3) the pro-aging PKH1/2 (Pkb-activating kinase homolog) pathway; (4) the anti-aging SNF1 (sucrose non-fermenting) pathway; (5) the anti-aging ATG (autophagy) pathway. Moreover, SCH9 is a pro-aging protein kinase stimulated by the TORC1 and PKH1/2 pathways, whereas RIM15 is an anti-aging protein kinase inhibited by the PKA and TORC1 pathways.

Each of the plant extracts exhibiting an extremely high anti-aging efficiency (as compare to the dietary restriction impact) was added to the different mutant cultures, at a concentration that was found to be optimal for its longevity-extending action.

Figure 4:
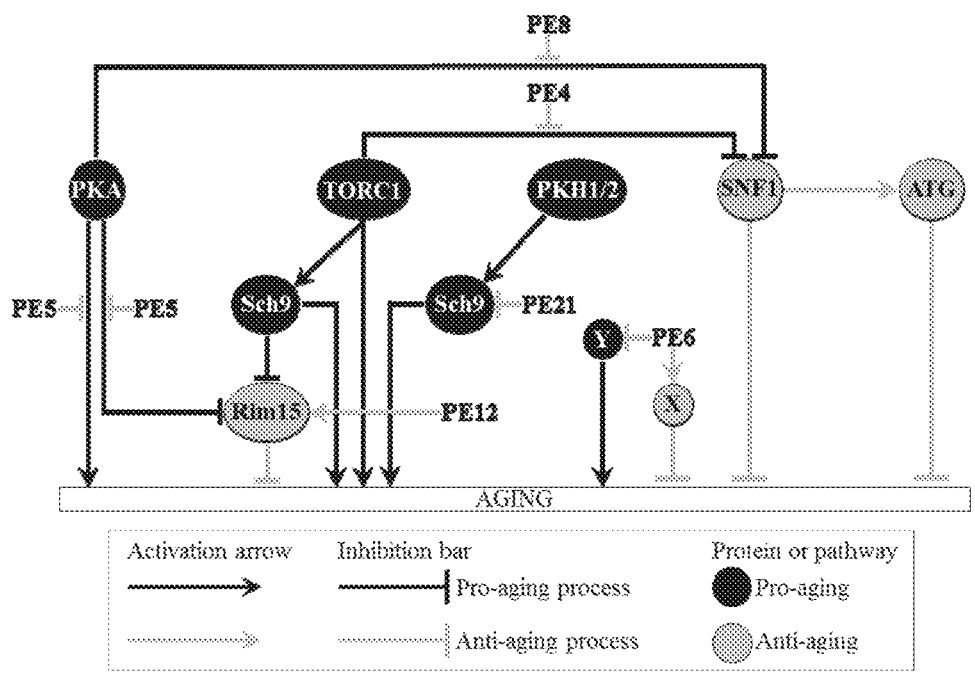
FIG. 4 illustrates how the Black cohosh extract (PE4), Valerian extract (PE5), Passion flower extract (PE6), *Ginkgo biloba* extract (PE8), Celery seed extract (PE12) and White willow extract (PE21) delay yeast chronological aging via the longevity-defining network of signaling pathways/protein kinases. Activation arrows and inhibition bars denote pro-aging processes or anti-aging processes.

These experiments revealed that certain plant extracts greatly delay aging by inhibiting only the pro-aging TOR signaling pathway, some plant extracts extend longevity by attenuating only the pro-aging cAMP/PKA signaling pathway, certain plant extracts delay aging by mitigating both the TOR and cAMP/PKA pathways, whereas some plant extracts extend longevity by targeting cellular processes that are not orchestrated by any of these two pro-aging signaling pathways (FIG. 4).

Figure 5:
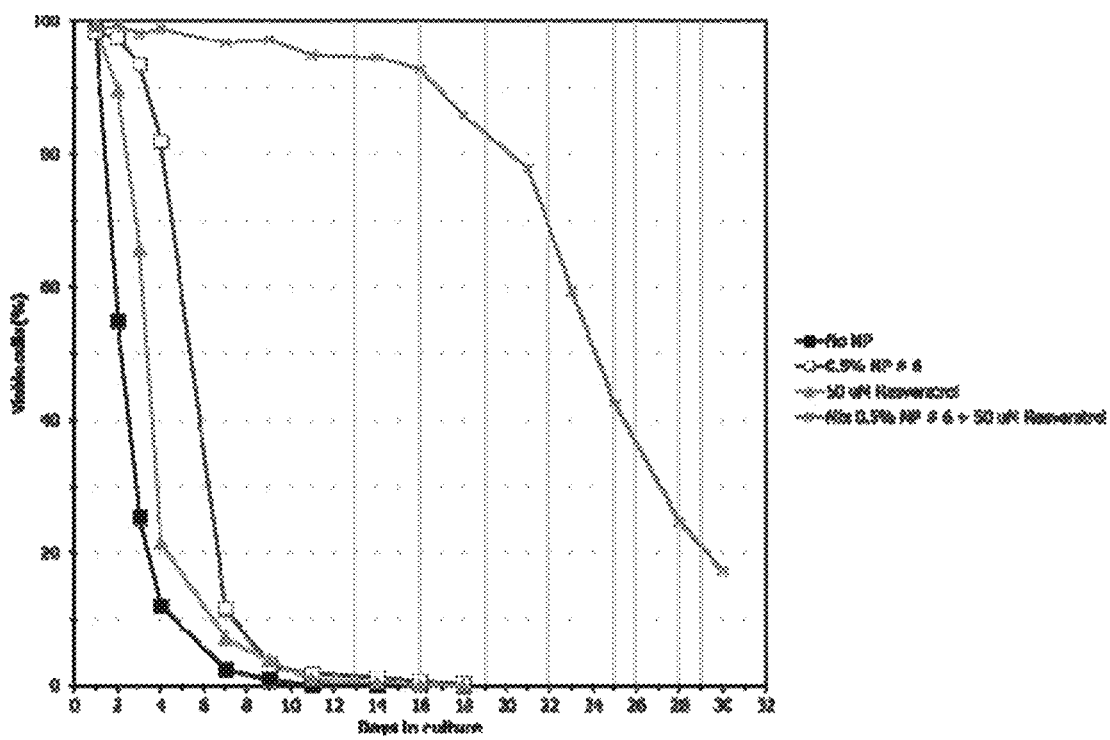
FIG. 5 illustrates the delaying of aging process by the synergy of a Passion flower extract (NP #6) with resveratrol.

Because passion flower extract (NP #6) and resveratrol target different pro- and anti-aging signaling pathways, their mixtures were expected to exhibit synergistic anti-aging effects. Indeed, a mixture of NP #6 and resveratrol exhibits a synergistic extending effect on longevity of yeast cells (FIG. 5). As this inhibitory effect on aging process is the most important ever seen, the analysis of cell lipids was done to have a better appreciation of this synergy.

The results of this experiment imply that Passion flower extract (NP #6) alone and together with resveratrol:
  i) Significantly increases the level of cardiolipin (this lipid can be found only in mitochondria), phosphatidylcholine, phosphatidylethanolamine, phosphatidylinositol;
  ii) Significantly decreases the level of the neutral lipid triacylglycerol; and
  iii) Does not change the levels of phosphatidic acid and phosphatidylserine.

None of these effects of an anti-aging compound has been reported before.

The present disclosure will be more readily understood by referring to the following examples which are given to illustrate embodiments rather than to limit its scope.

Example I

Identification of Previously Unknown Natural Anti-Aging Plant Extracts

The wild-type strain of the yeast *S. cerevisiae* BY4742 was cultured in a synthetic minimal YNB medium initially containing 2% glucose and supplemented with 20 mg/l histidine, 30 mg/l leucine, 30 mg/l lysine and 20 mg/l uracil. For assessing the longevity-extending efficiency of a plant extract, it was added at one of the following concentrations:
  concentration "0"—i.e., only ethanol, a solvent used as a vehicle for delivering various compounds into a cell, was added at a final concentration of 0.5%, 1.5%, 2.5% or 5%; and
  concentrations 0.1%, 0.3%, 0.5% or 1% of plant extract in 0.5%, 1.5%, 2.5% or 5% ethanol (final concentration), respectively.

Cells were cultured at 30° C. with shaking. A sample of cells was taken from a culture every day. A fraction of the sample was diluted in order to determine the total number of cells using a haemocytometer.

Another fraction of the cell sample was diluted and serial dilutions of cells were plated in duplicate onto plates with YP medium containing 2% glucose as carbon source. After 2 days of incubation at 30° C., the number of colony forming units (CFU) per plate was counted. The number of CFU was defined as the number of viable cells in a sample. For each culture, the percentage of viable cells was calculated as follows: (number of viable cells per ml/total number of cells per ml)×100. The percentage of viable cells in mid-logarithmic phase was set at 100%.

To quantitatively assess and compare the effects of various natural products added at different concentrations on longevity of chronologically aging yeast, the following two measures of chronological lifespan were calculated: (i) mean lifespan, the number of days required for a culture of yeast cells to reach 50% viability; and (ii) maximum lifespan, the number of days required for a culture of yeast cells to reach 10% viability (as show in FIG. 1). Each trial was done in triplicate and results are the average of the three trials.

A total of 31 plant extracts were selected as the one that may potentially have anti-aging effects. To test their potential anti-aging effects, these plant extracts were assessed for their efficiency to extend the chronological lifespan of the wild-type strain of the yeast *S. cerevisiae* BY4742. The table of the Example II resume the results for 6 'positive' extracts (i.e. the ones that significantly increase both the mean and maximum lifespans of yeast), whereas FIG. 2 demonstrates examples of 'negative' extracts. Among the 31 plant extracts tested, 6 extracts were found to be positive. More than 3500 trials were performed to identify such positive extracts, to establish their most efficient longevity-extending concentrations and to demonstrate the additive effects between their anti-aging effects (as discussed at Example III).

Example II

Plant Extracts from Different Commercial Sources Exhibit Similarly High Anti-Aging Effects To be sure that the extraction process is not a limitation, each of the 6 positive plant extracts was obtain from different commercial sources and assays was done like described in the Example I. Similar high anti-aging effects were seen with all commercial sources (Table 1). These data provide evidence that the extraction process and the commercial source are not limiting factors for the previously unknown potent anti-aging plant extracts described herein.

TABLE 1

Plant extracts from different commercial sources exhibit similarly high anti-aging effects.

| | Different commercial sources | | | | | | |
|---|---|---|---|---|---|---|---|
| Plant extracts | A mean/max lifespan (%) | B | C | D | E | F | G |
| Black Cohosh | 195/100 | similar | similar | | | | |
| Valerian | 185/87 | similar | similar | similar | similar | similar | similar |
| Passion flower | 180/80 | similar | similar | similar | similar | similar | similar |
| Ginkgo biloba | 145/104 | similar | similar | similar | similar | similar | similar |
| Celery seed | 160/107 | similar | similar | similar | | | |
| White willow | 475/369 | similar | similar | similar | similar | similar | similar |

Example III

Beneficial Effects Between Combinations of Different Plant Extracts

Because aging is known to be modulated by several signaling pathways that are controlled by different chemical compounds, the most efficient anti-aging approach is to use mixes of multiple natural products (such as plant extracts) that are capable of modulating different signaling pathways of longevity regulation. Some of these mixes are expected to provide improved beneficial effects when combined (i.e. mutually amplifying) effects on longevity. To identify the potential beneficial effects between the different combinations of anti-aging plant extracts presented at the Example I, different pairwise combinations of these extracts were tested.

For assessing the longevity-extending efficiency of each pair of one of the anti-aging plant extracts identified in Example I, each of them was added with another one at different concentrations. The different mixes of plant extracts were assessed for their effects on the chronological lifespan of WT strain of yeast. The pairwise mixtures of the following plant extracts extended the mean and maximum lifespans of chronologically aging yeast to significantly higher extent that each of the plant extracts alone. Table 2 show the best values obtained.

TABLE 2

Beneficial effects between combinations of different plant extracts

| Plant extracts | Alone (%) mean lifespan | Formulated with (%) | | | | | |
|---|---|---|---|---|---|---|---|
| | | 4 | 5 | 6 | 8 | 12 | 21 |
| Black Cohosh (4) | 195 | NA | 365 | 390 | 155 | 505 | 850 |
| Valerian (5) | 185 | 365 | NA | 385 | 375 | 510 | 775 |
| Passion flower (6) | 180 | 390 | 385 | NA | 320 | 365 | 865 |
| Ginkgo biloba (8) | 145 | 155 | 375 | 320 | NA | 495 | 665 |
| Celery seed (12) | 160 | 505 | 510 | 365 | 495 | NA | 570 |
| White willow (21) | 475 | 850 | 775 | 865 | 665 | 570 | NA |

NA = not applicable NTY = not tested yet

Example IV

Beneficial Effects Between Combinations of Different Plant Extracts and Well-Known Anti-Aging Chemical Compounds Currently known natural anti-aging compounds (resveratrol (Res), spermidine (Spe), metformin, and myriocin) delay aging in different organism, improve health and extend lifespan by targeting different longevity-defining cellular processes that are controlled by different signaling pathways. Therefore, as for Example III, it is plausible that if two or more of these compounds when added together, or with the anti-aging plant extracts of Example I, may exhibit an increase aging-delaying effect by enhancing the beneficial effect of each other on health and longevity. As for Example III, to identify the possible increased effects between the different anti-aging plant extracts presented in Example I and the currently known natural anti-aging compounds, their different combination was tested.

These different mixtures were assessed for their effects on the chronological lifespan of WT strain of yeast. It was observed that a synergistic anti-aging effect was noted when combining the Black Cohosh extract with Spermidine; Valerian extract with Resveratrol, metformin, myriocin and Spermidine; the Passion flower extract with Resveratrol, metformin, myriocin, and Spermidine; the Gingko *biloba* extract with Spermidine and myriocin; the Celery seed extract with Resveratrol, metformin and myriocin; and the White willow extract with Resveratrol, metformin, myriocin and Spermidine. The mixtures of the mentioned known natural anti-aging compounds and the newly identify anti-aging plant extracts as listed and identified hereinabove extended the mean and/or maximum lifespans of chronologically aging yeast to significantly higher extent that each of them alone.

Example V

Mass Spectrometry-Based Lipidomic Analyses of Yeast Cells Following Treatment with Passion Flower Extract Alone, Resveratrol Alone or with a Mixture of Passion Flower Extract and Resveratrol The wild-type strain of the yeast *S. cerevisiae* BY4742 (MATα his3Δ1 leu2Δ0 lys2Δ0 ura3Δ0) was cultured in a synthetic minimal YNB medium (0.67% Yeast Nitrogen Base without amino acids) initially containing 2% glucose and supplemented with 20 mg/l histidine, 30 mg/l leucine, 30 mg/l lysine and 20 mg/l uracil, as well as with a mixture of passion flower extract and resveratrol. Samples of cells were taken from a culture at days 1, 3, 6, 8 and 10 of culturing. Lipids were extracted from whole cells and then analyzed by quantitative mass spectrometry (see FIG. 5).

Example VI

Figure 6:
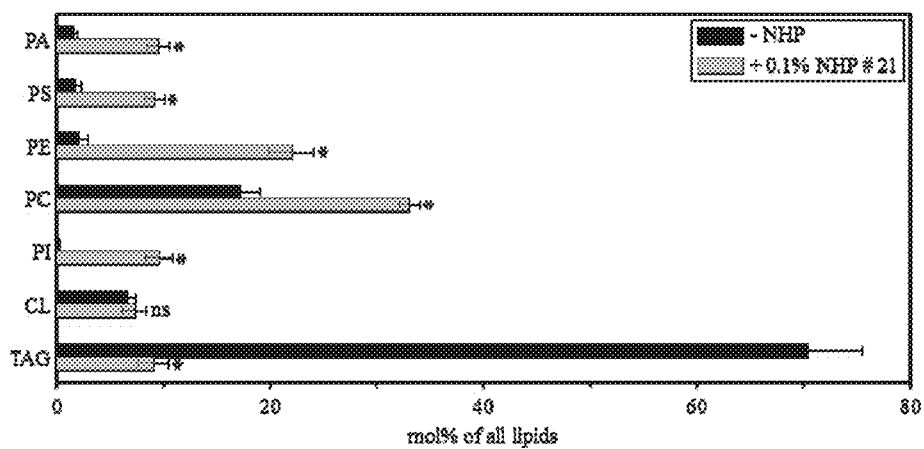
FIG. 6 illustrates the increase in cellular concentrations of phosphatidic acid (PA), phosphatidylserine (PS), phosphatidylethanolamine (PE), phosphatidylcholine (PC) and phosphatidylinositol (PI), the decrease in cellular concentration of triacylglycerols in chronologically aging yeast treated with the White Willow extract (NHP #21).

Specific Plant Extracts on Cellular Concentrations of Various Lipids in a Wild-Type Strain As a next step towards understanding mechanisms by which the newly identified aging-delaying extracts extend yeast longevity, a mass spectrometry (MS)-based quantitative analysis of many lipid classes was used to investigate how the six new anti-aging plant extracts influence cellular concentrations of various lipids in a wild-type strain. As an example the White Willow extract was found to: (1) considerably increase cellular concentrations of phosphatidic acid (PA), phosphatidylserine (PS), phosphatidylethanolamine (PE), phosphatidylcholine (PC) and phosphatidylinositol (PI), (2) greatly decrease cellular concentration of triacylglycerols (TAG; also known as fats); and (3) have no effect on cellular concentration of cardiolipin (CL) (FIG. 6). These findings suggest that the White Willow extract extends longevity of chronologically aging yeast by attenuating the synthesis of TAG (the major form of energy storage in yeast and other organisms, including humans) from diacylglycerol (DAG), PE and PC (FIG. 6).

Example VII

Extracts Slows the Progression of Yeast Chronological Aging by Differently Modulating Certain Cellular Processes As another step towards understanding mechanisms by which the newly identified aging-delaying extracts extend yeast longevity, different cellular processes were investigated. Each of the six longevity-extending plant extracts is a geroprotector which delays the onset and decreases the rate of yeast chronological aging by eliciting a hormetic stress response. Accordingly, each of these extracts slows the progression of yeast chronological aging by differently modulating certain cellular processes. These processes include mitochondrial respiration, maintenance of mitochondrial membrane potential, reactive oxygen species homeostasis, protection of cellular proteins and membrane lipids from oxidative damage, stabilization of mitochondrial and nuclear DNA, cell protection from chronic oxidative and thermal stresses, and lipolytic degradation of neutral lipids deposited in lipid droplets.

Figure 3:
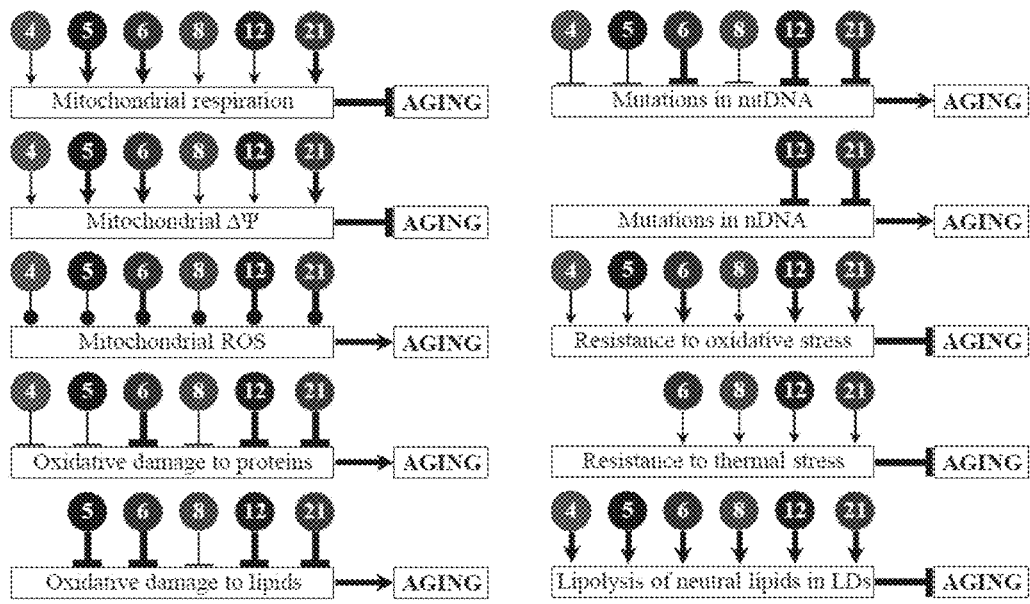
FIG. 3 illustrates a schematic representation of Black cohosh extract (PE4), Valerian extract (PE5), Passion flower extract (PE6), *Ginkgo biloba* extract (PE8), Celery seed extract (PE12) and White willow extract (PE21) delaying yeast chronological aging and have different effects on several longevity defining cellular processes. Arrows pointing at boxes with the terms of longevity-defining cellular processes denote activation of these processes, T bars denote inhibition of these processes, whereas lines with filled circles denote change in the age-related chronology of intracellular ROS. The thickness of such arrows, T bars and lines with filled circles correlates with the extent to which a PE activates, inhibits or alters the age-related chronology (respectively) of a particular longevity-defining cellular process. Arrows and T bars pointing at boxes with the term "AGING" denote acceleration or deceleration (respectively) of yeast chronological aging.

FIG. 3 presents the results. PE4 (Black Cohosh), PE5 (Valerian), PE6 (Passion flower), PE8 (*Ginkgo biloba*), PE12 (Celery seed) and PE21 (White willow) delay yeast chronological aging and have different effects on several longevity-defining cellular processes. Arrows pointing at boxes with the terms of longevity-defining cellular processes denote activation of these processes, T bars denote inhibition of these processes, whereas lines with filled circles denote change in the age-related chronology of intracellular ROS. The thickness of such arrows, T bars and lines with filled circles correlates with the extent to which a PE activates, inhibits or alters the age-related chronology (respectively) of a particular longevity-defining cellular process. Arrows and T bars pointing at boxes with the term "AGING" denote acceleration or deceleration (respectively) of yeast chronological aging. The characterisations of these processes are clear demonstrations of metabolic anti-aging impacts.

Example VIII

Extracts Slows the Progression of Yeast Chronological Aging by Different Mechanism of Action Aging of multicellular and unicellular eukaryotic organisms is a complex biological phenomenon affecting many cellular processes. These numerous cellular processes are modulated by signaling pathways that are conserved across phyla and converge into a network regulating longevity in evolutionarily distant organisms. In yeast, this network includes the following signaling pathways: (1) the pro-aging PKA (protein kinase A) pathway; (2) the pro-aging TORC1 (target of rapamycin complex 1) pathway; (3) the pro-aging PKH1/2 (Pkb-activating kinase homolog) pathway; (4) the anti-aging SNF1 (sucrose non-fermenting) pathway; (5) the anti-aging ATG (autophagy) pathway (FIG. 4). Moreover, SCH9 is a pro-aging protein kinase stimulated by the TORC1 and PKH1/2 pathways, whereas RIM15 is an anti-aging protein kinase inhibited by the PKA and TORC1 pathways (FIG. 4).

The effects of single-gene-deletion mutations eliminating different protein components of pro-aging and anti-aging signaling pathways were used to identify the mechanism of action of each anti-aging extract. This is an essential step towards understanding mechanisms by which the aging-delaying extracts extent longevity. This enable to identify a longevity-defining signaling pathway (or pathways) targeted by each of them.

FIG. 4 shows how PE4 (Black Cohosh), PE5 (Valerian), PE6 (Passion flower), PE8 (*Ginkgo biloba*), PE12 (Celery seed) and PE21 (White willow) extracts delay yeast chronological aging via the longevity-defining network of signaling pathways/protein kinases. Activation arrows and inhibition bars denote pro-aging processes or anti-aging processes.

Consequently, these extracts slow aging in the following ways: 1) plant extract 4 decreases the efficiency with which the pro-aging TORC1 pathway inhibits the anti-aging SNF1 pathway; 2) plant extract 5 mitigates two different branches of the pro-aging PKA pathway; 3) plant extract 6 coordinates processes that are not assimilated into the network of presently known signaling pathways/protein kinases; 4) plant extract 8 diminishes the inhibitory action of PKA on SNF1; 5) plant extract 12 intensifies the anti-aging protein kinase Rim15, and 6) plant extract 21 inhibits a form of the pro-aging protein kinase Sch9 that is activated by the pro-aging PKH1/2 pathway (FIG. 4).

Example IX

Synergy of the Six Extracts Together

Each of the six plant extracts (PEs) delays aging through different signaling pathways and/or protein kinases (FIG. 4, Example VIII). Therefore, this is why at the Example III, when these PEs are mixed in various combinations, some of the combinations display additive or synergistic effects on the aging-delaying efficiencies of each other. To see at which extend it's possible to increase the anti-aging impact, a trial was done in the same condition as in Example I, but at 0.1% of each extract. All together, these 6 extracts were able to extant the mean lifespan by 763%, which is better than any combination shown at Example III (Table 2).

Example X

Extracts Slows Aging Process and Improve Healthy Aging in Nematodes

Aging of multicellular eukaryotic organisms is a complex biological phenomenon affecting many cellular processes. Bristol N2 worms were used to test the impact of 2 extracts. Culture and handling of nematodes were conducted as previously described (Brenner et al., 1974, Genetics, 77: 71-94). Worms were maintained at 20° for all the experiments.

For lifespan assays, worms were synchronized by the alkaline hypochlorate method (Porta-de-la-Riva et al., 2012, J Vis Exp., 64: e4019). Synchronized L1 larvae were grown on bacteria to L4 larvae. At this stage, worms were seeded to plates containing the compound extracts or vehicle, which was considered day 1 of the experiment. Animals were considered dead when they ceased moving or responding to prodding. Animals that crawled off the plates, "exploded", or had a visible egl phenotype were discarded from the lifespan analysis.

Extract PE5 (Valerian) and PE8 (*Ginkgo biloba*) were tested and shown positive impact on longevity and vitality of nematodes. The nematodes were more active during the aging process. Extracts PE5 showed positive results at all the tested concentration (50, 100 and 250 ug/ml) and PE8 at the two most important concentrations (100 and 250 ug/ml).

Example XI

Extracts Slows Aging in Animal Accelerate Aging Model of Werner Syndrome

Werner syndrome (WS) is a human autosomal recessive disorder characterized by genomic instability, the premature aging and the onset of a number of age-related diseases. The defective enzyme responsible for WS possesses a 3'-5' exonuclease activity in addition to a 3'-5' DNA helicase activity and is involved in DNA repair, replication, transcription, and telomere maintenance. A mouse model was used with a deletion in the helicase domain of the murine WRN homologue that recapitulates many of the WS phenotypes, to test the anti-aging impacts of a mixture of plant extracts (a progeria model). The six anti-aging plant extracts described in this invention was added in animal water with resveratrol and olive polyphenols during a 12 months study.

After 12 months, animals were about 2 month younger considering their body weight. Glucose metabolism (fasting blood glucose and insulin, OGTT) was improved and kept as it was for 8 weeks animals. These two results, body weight and glucose metabolism, are related to a better energy usage regulation as seen for each extract as mitochondrial benefits. Their muscle resistance was greatly increased and underscores a possible utilization of these extracts in sarcopenia to conserve muscle during the aging process. This muscle impact is also related to a better energy metabolism and mitochondrial function during the aging process.

The memory was also slightly improved (maze test).

While the disclosure has been described in connection with specific embodiments thereof, it will be understood that it is capable of further modifications and this application is intended to cover any variations, uses, or adaptations, as may be applied to the essential features hereinbefore set forth, and as follows in the scope of the appended claims.

What is claimed is:

1. A method of delaying the onset of aging in a subject comprising administering to said subject a composition comprising at least two different anti-aging agents in an effective amount to achieve synergistic effect on delaying the onset of aging, wherein said at least two anti-aging agents have an superior effect on regulating longevity compared to one anti-aging agent, wherein said composition comprising:
a Black cohosh extract, a Valerian extract, a *Ginkgo biloba* extract, a Celery seed extract, a White willow extract and a Passion flower extract:
a Black Cohosh extract and Spermidine;
a Valerian extract with Resveratrol, metformin, myriocin or Spermidine
a passion flower extract and resveratrol, metformin, myriocin, or spermidine;
a *Gingko biloba* extract and myriocin or spermidine; or
a Celery seed extract and Resveratrol, metformin or myriocin.

2. The method of claim 1, wherein the composition modulates at least two pathways that regulate longevity.

3. The method of claim 2, wherein said pathways are TORC1, cAMP/PKA, PKH1/2, SNF1/AMPK or ATG pathways.

4. The method of claim 1, wherein said composition delays the onset and progression of age-related disorders.

5. The method of claim 4, wherein said age-related disorders are cardiovascular disorders, glycemic disorders, neurodegenerative disorders or osteoporosis disorders.

6. The method of claim 1, wherein the composition is formulated as a cosmetic composition, a dermatological composition, a nutraceutical composition or a pharmaceutical composition.

7. The method of claim 1, wherein the subject is a human, a mice or a nematode.

* * * * *